(12) United States Patent
Kim et al.

(10) Patent No.: US 9,995,741 B2
(45) Date of Patent: Jun. 12, 2018

(54) COMPLEX FOR DETECTING TARGET MATERIAL AND METHOD OF DETECTING TARGET MATERIAL USING THE SAME

(71) Applicant: GWANGJU INSTITUTE OF SCIENCE AND TECHNOLOGY, Gwangju (KR)

(72) Inventors: Min-Gon Kim, Gwangju (KR); Eun-Jung Jo, Gwangju (KR); Hyo-Young Mun, Gwangju (KR)

(73) Assignee: GWANGJU INSTITUTE OF SCIENCE AND TECHNOLOGY, Gwangju (KR)

( * ) Notice: Subject to any disclaimer, the term of this patent is extended or adjusted under 35 U.S.C. 154(b) by 0 days. days.

(21) Appl. No.: 15/229,913

(22) Filed: Aug. 5, 2016

(65) Prior Publication Data

US 2017/0038375 A1 Feb. 9, 2017

(30) Foreign Application Priority Data

Aug. 6, 2015 (KR) ........................ 10-2015-0110936

(51) Int. Cl.
 C07H 21/02 (2006.01)
 C07H 21/04 (2006.01)
 A61K 48/00 (2006.01)
 G01N 33/542 (2006.01)
 G01N 21/00 (2006.01)
 G01N 33/58 (2006.01)

(52) U.S. Cl.
 CPC ........... G01N 33/542 (2013.01); G01N 21/00 (2013.01); G01N 33/587 (2013.01); G01N 2333/37 (2013.01)

(58) Field of Classification Search
 CPC .. C12N 15/111; C12N 15/113; C12N 2310/11
 See application file for complete search history.

(56) References Cited

U.S. PATENT DOCUMENTS

| | | | |
|---|---|---|---|
| 2009/0081808 A1* | 3/2009 | Burmeister et al. . | C12N 15/113 |
| 2009/0105172 A1* | 4/2009 | Diener et al. ........ | C12N 15/113 |
| 2012/0190015 A1* | 7/2012 | Cruz-Aguado et al. .................... | C12N 15/113 |
| 2014/0128588 A1* | 5/2014 | Hargreaves .......... | C12N 15/115 536/23.1 |
| 2014/0335630 A1* | 11/2014 | Cameron ........... | G01N 33/5308 436/501 |
| 2015/0362500 A1* | 12/2015 | Anker ................ | A61K 49/0423 424/9.42 |

FOREIGN PATENT DOCUMENTS

| KR | 10-2013-0005757 A | 1/2013 | |
|---|---|---|---|
| KR | 10-2015-0080417 A | 7/2015 | |
| WO | WO 2011/063356 A3 * | 5/2011 | ........... C12N 15/113 |

OTHER PUBLICATIONS

Eun-Jung Jo et al., Homogeneous Biosensor for Target Molecule Detection Based on Luminescence Resonance Energy Transfer Using the Upconversion Nanoparticlesn, Nano Korea 2015 Symposium, Jul. 1, 2015, Total 3 pages.

* cited by examiner

Primary Examiner — Amy H Bowman
(74) Attorney, Agent, or Firm — Hauptman Ham, LLP

(57) ABSTRACT

The present disclosure relates to a complex for detecting a target material comprising upconverting nanoparticles; and at least one target material specific aptamer-quencher, connected through a linker with the upconverting nanoparticles, a method of preparing the same, a kit for detecting a target material comprising the same, and a method of detecting a target material using the same.

According to the present disclosure, different target materials in samples can be quantified or detected accurately based on luminescence resonance energy transfer (LRET) of the upconverting nanoparticles (UCNPs) excited by a near infrared (NIR) light source.

15 Claims, 15 Drawing Sheets

(Plan view of portable equipment)

(Stereoscopic view of portable equipment)

COMPLEX FOR DETECTING TARGET MATERIAL AND METHOD OF DETECTING TARGET MATERIAL USING THE SAME

CROSS REFERENCE TO RELATED APPLICATION

This application is based upon and claims the benefit of priority from Korean Patent Application No. 10-2015-0110936, filed on Aug. 6, 2015 in the Korean Intellectual Property Office, the entire contents of which are incorporated herein by reference.

BACKGROUND

1. Technical Field

The present disclosure relates to a complex for detecting a target material and a method of detecting a target material using the same. More specifically, the present disclosure is directed to a complex for detecting a target material comprising upconverting nanoparticles (UCNPs) excited by a near infrared (NIR) light source and a target material specific aptamer-quencher, a method of preparing the same, a kit for detecting a target material comprising the same, and a method of detecting a target material using the same.

2. Description of the Related Art

Recently, detecting a target material such as mycotoxins present in a sample has been emerging as an important issue.

One of the mycotoxins of these target materials is Ochratoxin A (OTA). OTA is a mycotoxin that is produced by several fungal strains of *Aspergillus* and *Penicillum* genera, and primarily exists in for example coffee, grains, legumes, wine, grape juice, and the like. OTA has been reported not to be destroyed by cooking process such as a common heat treatment, but has a chemical stability and long half-life and induces DNA damages and chromosomal abnormalities. OTA has been classified by the International Agency for Research on Cancer as being a possible carcinogen in humans with the characteristics of teratogenicity, carcinogenicity, immune toxicity, hepatotoxicity, etc. (Group 2B). Due to potential risks to human health and possible contaminations of various foods, many countries enacted a regulatory limit for the levels of OTA for specific foods, and several research efforts have been conducted to develop sensitive methods for OTA detection.

Standard detection method according to the Association of Official Agricultural Chemists (AOAC) includes a high-performance liquid chromatography (HPLC). Although this method provides a high sensitivity, since it has to undergo processes including washings or analysis such as by extraction, cartridge and/or immune-affinity column, the detection process is complicated, and thereby requires a specialist and takes a long time in analysis, as well as costs high. As an alternative to overcome these drawbacks, there includes an enzyme immunoassay (ELISA) and a lateral flow immunoassay (LFA). However, the ELISA frequently causes a used antibody to be cross-reactive with materials similar to the Ochratoxins, and therefore the accuracy is poor. Thus, the ELISA has not yet been used as an internationally recognized method (AOAC). Further, with the ELISA and LFA, it is not easy to acquire antibodies for detecting a low molecular material, Ochratoxins, and since they receive a negative signal by an immune response through a competitive reaction, the sensitivity is not good. In particular, when applying to a real food sample, homogeneous detection of OTA is limited due to a matrix effect caused by by-products in various foods.

Additionally, methods of using a biosensor based on fluorescence resonance energy transfer (FRET) are disclosed. According to the FRET method, it is advantageous that a combination of a target material can be measured in a homogenous state without a washing process. However, it is problematic that biomolecules may be damaged by UV or visible light used to excite organic fluorescent materials and quantum dots, and non-specific signals may be caused by matrix effects due to different by-products discharged from samples.

SUMMARY

It is an aspect of the present disclosure to provide a complex for detecting a target material which can homogeneously detect a target material by removing a matrix effect due to different by-products present in a sample, shorten an analysis time through a simple detection process, reduce a detection cost, and be utilized for detecting a variety of target materials; and a method of preparing the same; a kit for detecting a target material comprising the same; and a method of detecting a target material using the same.

The present disclosure is not limited to the above aspect and other aspects of the present disclosure will be clearly understood by those skilled in the art from the following description.

In accordance with a first embodiment of the present disclosure, a complex for detecting a target material including upconverting nanoparticles; and at least one target material specific aptamer-quencher, connected through a linker with the upconverting nanoparticles is provided.

In accordance with a second embodiment of the preset disclosure, a kit for detecting a target material including the complex for detecting a target material is provided.

In accordance with a third embodiment of the present disclosure, a method of detecting a target material, including: connecting a sample with the complex for detecting a target material; and irradiating a near-infrared light source to the complex in contact with the target material in the sample and measuring a degree of attenuation of an eminent signal of the upconverting nanoparticles is provided.

In accordance with a fourth aspect of the present disclosure, a method of producing a complex for detecting a target material, including: preparing a linker-aptamer-quencher; modifying a surface of upconverting nanoparticles with a carboxyl group; and binding the carboxyl group and a terminal amine group of the linker-aptamer-quencher is provided.

According to the present disclosure, different target materials in samples can be quantified or detected accurately based on luminescence resonance energy transfer (LRET) of the upconverting nanoparticles excited by a near infrared (NIR) light source.

DETAILED DESCRIPTION

Figure 1:
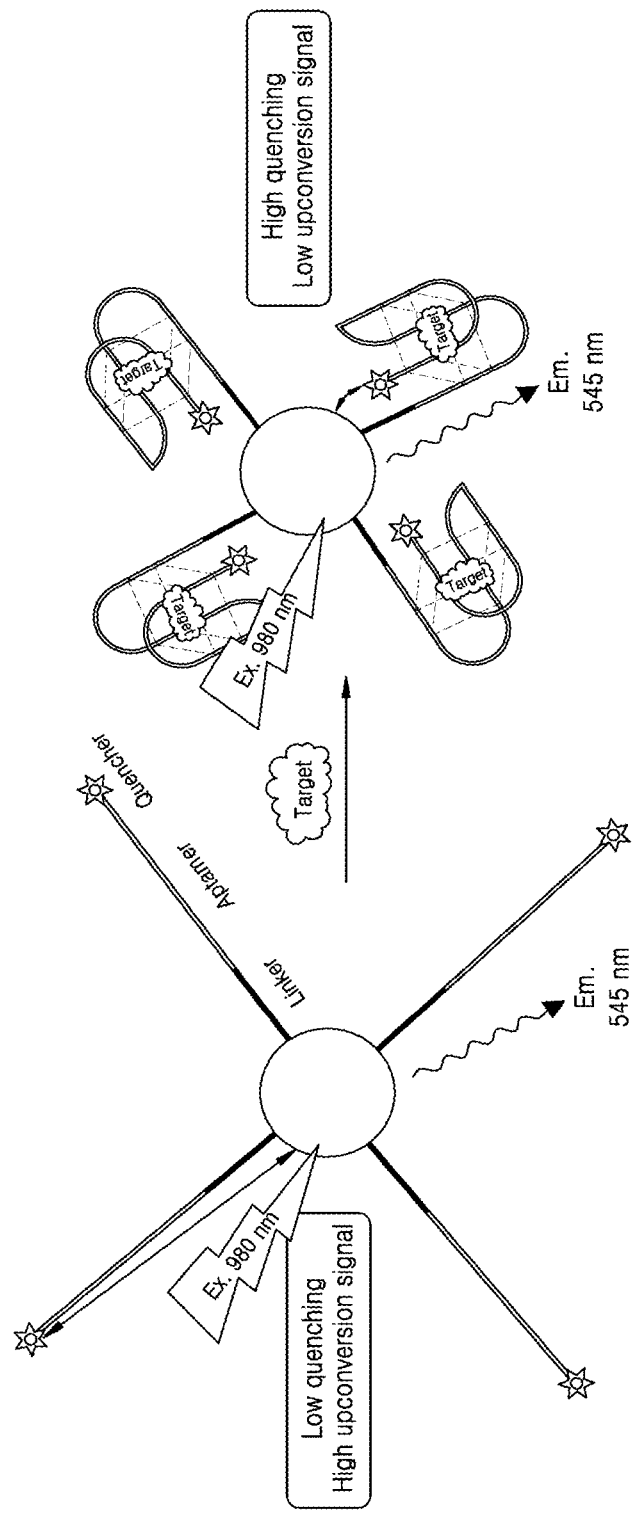
FIG. 1 is a schematic illustration of the process where the luminescence resonance energy transfer takes place from upconverting nanoparticles to a quencher becoming closer due to a structural folding of an aptamer by a target material in accordance with an embodiment of a complex including the upconverting nanoparticles/aptamer-quencher.

Hereinafter, embodiments of the present disclosure will be described in detail with reference to the accompanying drawings. It should be understood that the present disclosure is not limited to the following embodiments, and that the embodiments are provided for illustrative purposes only. The scope of the disclosure should be defined only by the accompanying claims and equivalents thereof.

As used herein, the terms "comprise," "comprising," "include," "including," and "includes" are intended to specify the presence of stated features, integers, components, or steps, but they do not preclude the presence or addition of one or more other features, integers, components, steps, acts, or groups.

As used herein, the term "about" or "substantially" is intended to have meanings close to numerical values or ranges specified with an allowable error and intended to prevent accurate or absolute numerical values disclosed for understanding of the present disclosure from being illegally or unfairly used by any unconscionable third party. As used herein, the term "step of" does not mean "step for."

As used herein, the term "combination(s) thereof" included in Markush type description means mixture or combination of one or more components, steps, operations and/or elements selected from a group consisting of components, steps, operation and/or elements described in Markush type and thereby means that the disclosure includes one or more components, steps, operations and/or elements selected from the Markush group.

Further, as used herein, the terms "first," "second," and the like do not denote any order, quantity, or importance, but rather are used to differentiate one element from another. Thus, a first element, component, region, layer or section discussed below could be termed a second element, component, region, layer or section without departing from the teachings of the present disclosure, and vice versa.

As used herein, the term "target material" refers to a material that is present in a sample and capable of being quantified or detected through binding with an aptamer. The target material is not particularly limited as long as it can be quantified or detected by binding with an aptamer, and includes for example fungal toxins, cells, proteins, nucleic acids, compounds, and combinations thereof.

As used herein, the term "aptamer" refers to a single-strand nucleic acid (e.g., DNA, RNA or a modified nucleic acid) that can be specifically bound to a target material to be detected in a sample and has a stable tertiary structure in itself, through a specific binding of which the presence of the target material in the sample can be confirmed. The aptamer may be made by synthesizing oligonucleotides having a selective and high affinity for a target material to be identified according to a common method of preparing the aptamer, and modifying 5' terminus or 3' terminus of the oligonucleotides to —SH, —COOH, —OH or —NH$_2$ such that the terminus can be bonded to a functional group of a linker.

As used herein, the term "sample" refers to a material that is expected to contain a target material to be detected, including, but not limited to, foods, tissues, cells, whole blood, serum, plasma, saliva, sputum sample, cerebrospinal fluid, or urine.

As used herein, the term "detecting" and the like refers to a behavior to determine the presence or absence of a target material in a sample.

In the present disclosure, in order to detect mycotoxins in foods or various biomarkers in samples, there is intended to provide a platform based on luminescence resonance energy transfer (LRET) of upconverting nanoparticles excited by a near infrared (NIR) light source.

To this end, one embodiment of the present disclosure provides a complex for detecting a target material and a detection kit comprising the complex, particularly, the complex comprising (i) upconverting nanoparticles; and (ii) at least one target material specific aptamer-quencher, connected through a linker with the upconverting nanoparticles.

The upconverting nanoparticles are those which absorb a light in a near-infrared region due to a sequential absorption of two or more photons, and emit a light at a shorter wavelength region of ultraviolet or visible light than an excitation wavelength. The upconverting nanoparticles have the characteristics of greater signal strength of light emission, excellent stability and biocompatibility, and can adjust the wavelength of eminent signal by controlling the type and concentration of a host, an activator, or a sensitizer.

In particular, since a near-infrared light is used when exciting the upconverting nanoparticles, the aptamer for detecting a target material and the target material can be prevented from damaging. Further, it is possible to prevent the decrease of the detection signal and the non-specific reactions due to matrix effects caused by a variety of by-products present in an actual sample.

Figure 3:
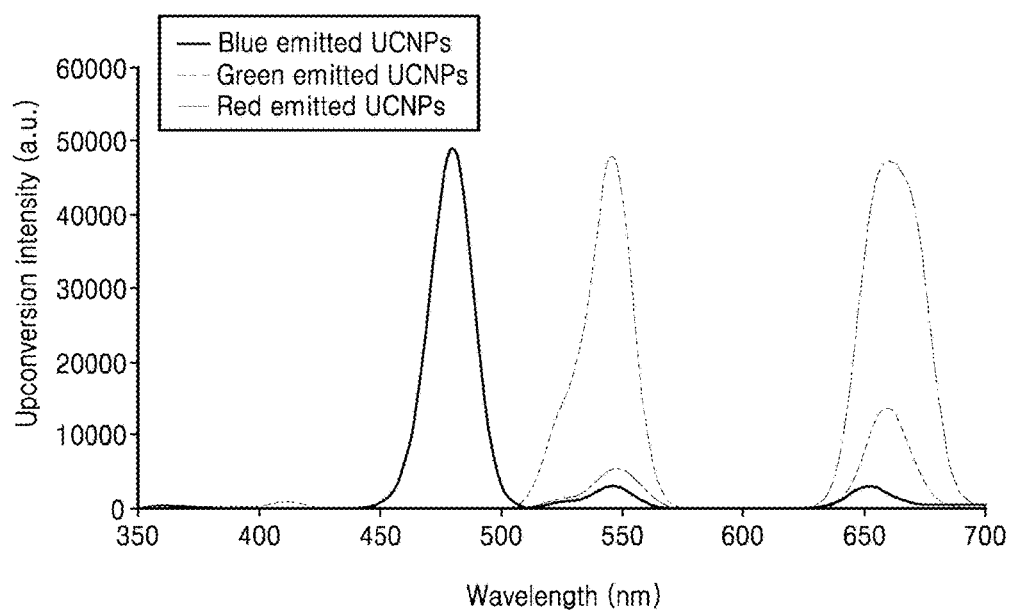
FIG. 3 shows spectra of lights emitted under the irradiation of near infrared 900 nm diode laser to the upconverting nanoparticles synthesized in accordance with an embodiment of the present disclosure.

The upconverting nanoparticles include as a primary component a rare earth element. As a specific example, the upconverting nanoparticles may include at least one selected from yttrium (Y) and ytterbium (Yb), and at least one activator selected from erbium (Er), holmium (Ho), and thulium (Tm). The composition may be variously adjusted under NIR irradiation to synthesize nanoparticles having various wavelength bands, as depicted in FIG. 3. In general, when synthesizing the upconverting nanoparticles, the concentration of the activator such as erbium (Er), holmium (Ho), or thulium (Tm) may be 10 times lower than that of ytterbium (Yb) used as the sensitizer, but is not necessarily limited thereto.

According to a specific embodiment, the upconverting nanoparticles may have Formula 1, 2, or 3 below, but without limitation can have more various compositions. Further, different concentration ratios of the sensitizer and the activator can be set.

$NaYF_4$: 20% Yb3+, 2% Er3+ [Formula 1]

$NaYF_4$: 20% Yb3+, 2% Ho3+ [Formula 2]

$NaYF_4$: 20% Yb3+, 2% Tm3+ [Formula 3]

Surfaces of the upconverting nanoparticles can be modified to form upconverting nanoparticles-aptamer complex. Since the synthesized upconverting nanoparticles are hydrophobic, it is essential to modify the surface to be well dispersed in water in order to combine various aptamers for detecting a target material. A method for the surface modification may include an encapsulation of the upconverting nanoparticles by polyethylene glycol (PEG), and a coating thereof with silica. The upconverting nanoparticles may have an average diameter of about 25 nm to 30 nm. The silica-coated and PEG-encapsulated upconverting nanoparticles can be reactive with a near-infrared light and well dispersed in an aqueous solution to form a coupling with a biological substance.

Thus, the surface-modified upconverting nanoparticles can be used to form the upconverting nanoparticle/aptamer-quencher complex, such that a variety of aptamer-quencher can, without limitation, be fixed to the upconverting nanoparticles. At least one of the fixed aptamer-quencher may be selected based on a type of the target material. The sequence of the aptamer may vary depending on the type of the target material. When various types of target materials are diagnosed at the same time, upconverting nanoparticles having different light emitting wavelengths and a quencher having absorption wavelength similar to the light emitting wavelength can be used. Therefore, a quencher having a proper absorption wavelength can be selected to be coupled with an aptamer, wherein the quencher can be introduced during the synthesis of the aptamer, or be introduced by modifying the terminal of the aptamer to a specific functional group and subsequently chemically bonding it with a quencher having a functional group that is associative therewith.

For example, if phosphoramidite monomer with which a quencher is coupled instead of Guanine (G), Adenine (A), Thymine (T), and Cytosine (C) during a coupling step in the synthesis of the aptamer, the quencher may be introduced to the terminal of the aptamer. Alternatively, as non-limiting examples, the quencher may be introduced to the terminal of the aptamer by modifying the terminal of the aptamer with an amine group, and then reacting with n-hydroxysuccinimide (NHS)-quencher, without being limited thereto.

Figure 9:
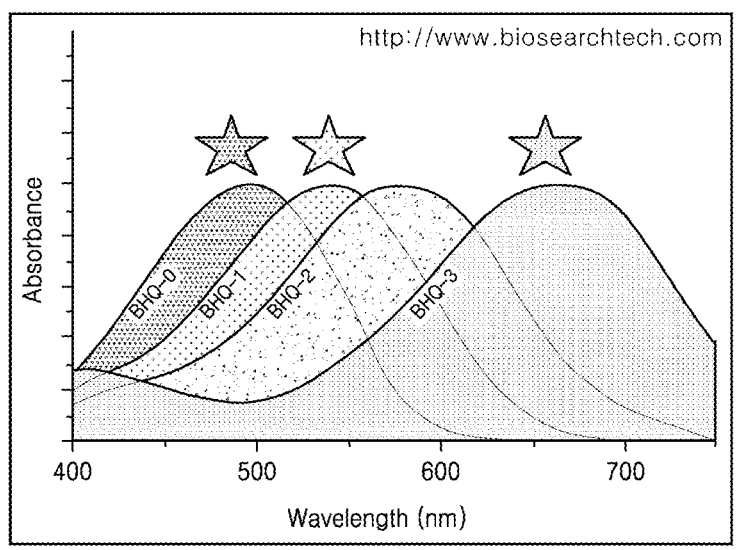
FIG. 9 shows an absorbance (quenching) wavelength and a maximum absorbance wavelength for different quenchers in accordance with an embodiment of the present disclosure.

The quencher may include at least one selected from the group consisting of blackhole quenchers (BHQs), organic fluorescent minerals, and quantum dots (Q-dots). FIG. 9 shows exemplary types of quenchers and the absorption (quenching) wavelength regions thereof that can be used in the present disclosure.

The aptamer-quencher is connected via said upconverting nanoparticles and linker, wherein the linker may be introduced to one end of the aptamer, similarly to the process of introducing the aptamer into the quencher. That is, by controlling the number of meaningless sequence such as adenine (A) at the time of synthesizing the aptamer, the linker may be bonded to one terminal of the aptamer. The number of the linker is preferably controlled to have a proper length, such that the linker is formed on one end of the aptamer to which the quencher is not bound and therefore the energy transfer can take place effectively.

The upconverting nanoparticles and the linker-aptamer-quencher can be connected via a physical or chemical bonding of the functional groups of the upconverting nanoparticles whose surfaces are modified and the terminal functional groups of the linker-aptamer-quencher. The chemical bonding may include for example a covalent bond, ionic bond, etc. The physical binding may include for example adsorption. The linker-aptamer-quencher can have at its one side terminal (5') a functional group that is capable of binding to the upconverting nanoparticles, and can include at the other side terminal (3') a quencher that can absorb the emission energy of the emitted upconverting nanoparticles. The 5' terminal and 3' terminal are intended to merely distinguish the two ends to each other, and thus if the one side end is 5' terminal, then the other end is 3' terminal, and if on side end is 3' terminal, then the other end is 5' terminal.

The up-converting nanoparticles of the complex can serve as an energy donor, and the quencher having an absorption wavelength in a region similar to the light emitting wavelength of the donor under the near-infrared irradiation can serve as an energy acceptor. At this time, a luminescence resonance energy transfer takes place from the donor to the acceptor through a specific binding of the aptamer and the target material in the upconverting nanoparticles/aptamer-quencher. With the increase in the concentration of the target material to be detected, the strength of the eminent signals of the up-converting nanoparticles will be more and more reduced. That is, it is possible to detect the target material quantitatively through the attenuated eminent signals. The distance between the quencher and the upconverting nanoparticles becomes closer by a specific binding of the aptamer to which the quencher is bound having an absorption wavelength region overlapped with some or whole of the emitted wavelength region of the upconverting nanoparticles with the target material. Accordingly, it is possible to effectively detect various target materials by attenuated eminent signals through the luminescence resonance energy transfer. If necessary, it is possible to select different types of the upconverting nanoparticles so as to vary the emitted wavelength region.

As shown in FIG. 1, when the complex for detecting a target material is irradiated with a near infrared light, the excited luminescence resonance energy of the upconverting nanoparticles, which is a donor, is transferred to the quencher of the terminal of the aptamer, which is an acceptor. Accordingly, it is advantageous in terms of energy transfer that the emitted wavelength region of the upconverting nanoparticles is overlapped with the absorption wavelength region of the quencher constituting the aptamer-quencher either in part or wholly. At this time, the aptamer-quencher is connected via said upconverting nanoparticles and the linker, wherein when the aptamer is structurally folded by a target material, the distance between the upconverting nanoparticles and the quencher becomes closer, such that the energy transfer can easily be facilitated. The target material can be detected through the attenuated eminent signal due to the energy transfer.

The aptamer is specific to a target material present in real samples (foods or a specimen). When the target material is absent, the upconverting nanoparticles do not cause the attenuation of the eminent signal, leading to a higher up-converted signal, whereas when the target material exists, the structural changes in the aptamer by the target material causes the attenuation of the eminent signal, leading a lower up-converted signal.

For the purpose of the present disclosure, the aptamer may be, as one example, a DNA at one end of which an amine group ($-NH_2$) is combined, but not limited thereto.

The aptamer may be freely selected according to the target material. Therefore, if it is intended to select a variety of target materials, since each of the aptamers specific to these target materials can be selected, an aptamer-quencher that can be connected through a linker to the upconverting nanoparticles may be at least one. In other words, at least one aptamer-quencher selected according to the type of the target material may be connected to the upconverting nanoparticles. In addition, the aptamer-quencher may be specific to the at least one target material.

It is preferable for the upconverting nanoparticles to maintain an appropriate distance with the aptamer, which is achievable by a connection using a linker. It is important to adjust the length of the linker in order to find an optimum distance where the energy transfer from an energy donor to an energy acceptor can take place efficiently. If the linker is too long, the distance between the donor and the acceptor is too far, and then the energy transfer cannot be done effectively. Therefore, it is important to select an appropriate length of the linker and therefore it is expected to optimize the degree of attenuation of the eminent signals by adjusting the length of the linker. In this respect, the use of a chemical linker is advantageous. For example, the length of the liker can be adjusted by inserting Adenine, Thymine, Cytosine, PEG (polyethylene glycol), etc., and adjusting the number thereof.

Preferably, a functional group introduced into a terminal portion of the liker can be bound with a functional group introduced into the upconverting nanoparticles. In other words, physical or chemical bonding between the functional groups can form a complex. It is noted that the absence of the linker (denoted as '0') indicates the introduction of an amine group at 5' position at which the aptamer sequence is terminated.

Terminal functional group of the aptamer (5') containing the linker is combined with the functional group of the upconverting nanoparticles through the following process. It is understood that the aptamer mentioned in relation to the formation of a bonding of the aptamer and the upconverting nanoparticles includes the presence or absence of the linker, as hereinbelow simply denoted as aptamer.

Among the chemical bonds, specifically the covalent bonds can be formed as below, and therefore the combination of an aldehyde group introduced into a surface of the upconverting nanoparticles and a target material specific aptamer can be made by the steps below:

(A) coating a silica on the upconverting nanoparticles, (B) introducing an amine group into the silica on which the upconverting nanoparticles are coated, (C) converting the amine group to an aldehyde group, and (D) binding the aldehyde group and a terminal amine group of the aptamer.

In this embodiment, the step (A) may be carried out by reacting the upconverting nanoparticles with tetraethyl orthosilicate. The step (B) may be performed using an aminopropyl trimethoxy silane. The step (C) may be carried out using a glutaraldehyde. Further, the step (D) may be conducted by forming a Schiff base structure with the terminal amine group of the aptamer and the amine group of the ligand, and the aldehyde group of the upconverting nanoparticles, as shown in reaction scheme 2 below.

[Scheme 2]

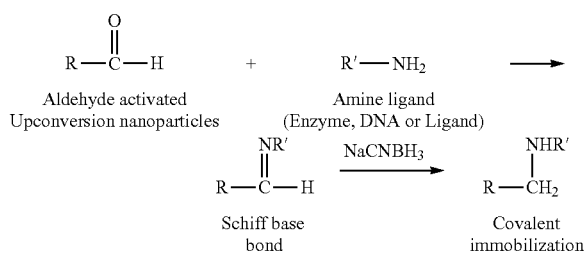

Further, the covalent bond can be achieved by a combination of the epoxy group introduced into the surface of the upconverting nanoparticles and the aptamer, which may specifically be made by the steps below:

(A) coating a silica on the upconverting nanoparticles, (B) introducing an epoxy group into the silica on which the upconverting nanoparticles are coated, and (C) binding the epoxy group with an amine group of the aptamer. In addition, in step (C), the epoxy group may be bound with a terminal amine group or thiol group of the aptamer, or an amine group of the ligand.

The step (A) may be carried out by reacting the upconverting nanoparticles with tetraethyl orthosilicate. The step (B) may be performed using a glycidoxypropyl trimethoxy silane. Further, the step (C) may be performed by forming a covalent bond of a terminal amine group or thiol of the aptamer, or an amine group of the ligand with an epoxy group of the upconverting nanoparticles, as shown in reaction schemes 3 and 4.

[Scheme 3]

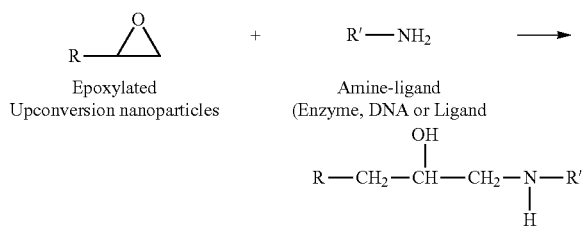

[Scheme 4]

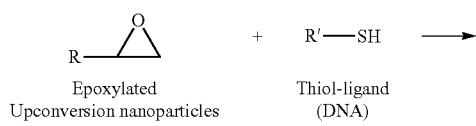

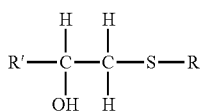

In addition, the covalent bond may be achieved by a combination of a carboxyl group introduced into the surface of the upconverting nanoparticles and the aptamer, specific details of which will be described later.

The combination is an amide bond between the carboxyl group introduced into the surface of the upconverting nanoparticles and the terminal amine group of the aptamer. As a specific example, the bond is obtained by the reaction between 1-ethyl-3-(3-dimethylaminopropyl) carbodiimide (EDC) and hydroxyl succinimide (NHS).

More specifically, the carboxyl groups are activated by adding EDC to the carboxylated silica-coated upconverting nanoparticles. That is, EDC is added to activate the reaction to form an unstable intermediate, which is not included in a final complex structure. Then, NHS is added to form an NHS-ester bond. After such EDC/NHS reaction, aptamer-quencher containing a linker is added to form an amide bond with a terminal amine group of the aptamer containing the linker, which leads to a stable covalent bond, thereby forming a complex comprising the upconverting nanoparticles-(linker)-aptamer-quencher.

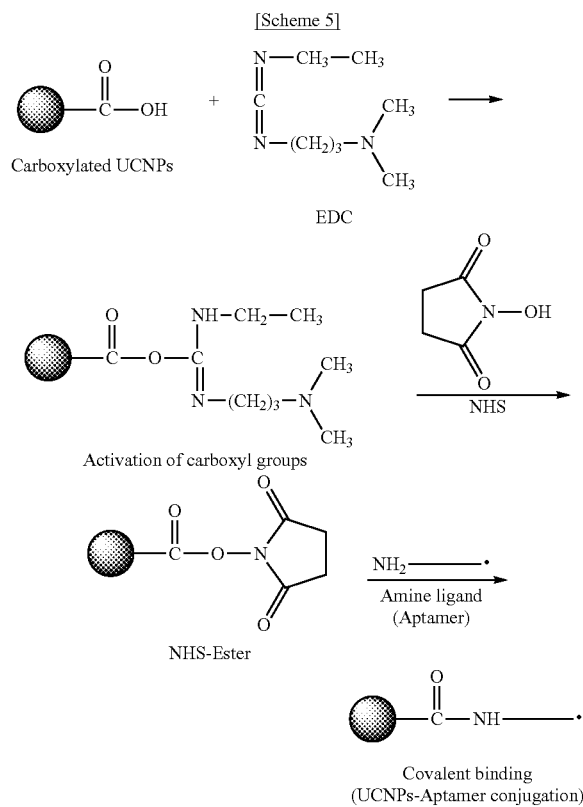

According to another embodiment of the present disclosure, the surface of the upconverting nanoparticles may be modified by a silica coating or a polyethylene glycol (PEG) encapsulation method.

The silica coating or PEG encapsulation is a method for introducing a functional group into the upconverting nanoparticles to form a complex with the aptamer. In the case of the silica coating, as noted above, after silica coating, an aldehyde group, an epoxy group, or a carboxyl group is introduced, specific details of which are as described above.

On the other hand, carboxyl groups may be introduced by the PEG encapsulation of the upconverting nanoparticles. At this time, the upconverting nanoparticles are surrounded by using PEG-phospholipids to form a micelle structure, such that the upconverting nanoparticles which are well dispersed in water and show carboxyl groups can be obtained.

Specifically, the upconverting nanoparticles are mixed with 1,2-dimiristoyl-sn-glycero-3-phosphoethanolamine-N-[methoxy(polyethylene glycol)-2000] (mPEG (2000)) and 1,2-distearoyl-sn-glycero-3-phosphoethanolamine-N-[carboxy(polyethanolglycol)-2000] (DSPE-PEG (2000) Carboxylic Acid) and stirred, and then a reaction solvent is evaporated and washed.

In addition to the covalent bonds described above, the upconverting nanoparticles can be bound with the aptamer specific to a target material through a non-covalent bond such as an ionic bond or adsorption.

Examples of such non-covalent bond may include the use of bonding with a protein such as avidin, streptavidin, or neutravidin, and a chemical substance such as biotin. Such bonding is known to have a very high affinity, as reaction with an antibody and an antigen.

This bonding can be viewed as the combinatorial result of a number of causes. Firstly, there may be mentioned as one of those causes a highly complementary shape between a binding pocket of the above protein and a biotin. Secondly, a huge network of hydrogen bonds formed when a biotin is present in the above binding site may be viewed as one of those causes. Finally, since the binding pocket to which a biotin is attached is hydrophobic, when it is at the binding site, the Van der Waals attraction formed by a hydrophobic interaction produced by the biotin may be one of those causes.

Thus, the upconverting nanoparticles can be combined with the amine of the proteins listed above to form a complex of the upconverting nanoparticles and the proteins listed above, while after bonding a biotin to a terminal of the aptamer, the upconverting nanoparticles/aptamer-quencher can be formed using the bonding mentioned above.

According to another embodiment, the average diameter of the upconverting nanoparticles is from 25 nm to 30 nm.

In bonding a target material specific aptamer and carrying out the washing and reaction, if the size of the upconverting nanoparticles exceeds the upper limit of the above range, there is a possibility to precipitate, whereas if the size is less than the lower limit thereof, the effect of this disclosure cannot sufficiently be provided.

According to an aspect of the present disclosure, a kit for detecting a target material comprising a complex of a target material specific aptamer-quencher to which a surface-modified upconverting nanoparticles and the quencher are attached. Preferably, such kit is provided in a form of biochip by fixing a composition comprising the complex to a substrate, or provided in a form of filled column, but not limited thereto. Further, the kit may be provided in such a form that the complex is contained in a container.

Within such kit, near-infrared light source may be further contained. The near infrared light source may include a diode laser having a wavelength of 980 nm.

In addition, the kit may additionally contain a detector. The detector has the ability of measuring an emission intensity of the complex before sample treatment, and an emission intensity of the complex after sample treatment, respectively.

In addition, the kit may further include a computing unit that can calculate the degree of attenuation of the emission intensity of the complex after sample treatment based on the emission intensity of the complex itself by receiving both the emission intensity of the complex before sample treatment and the emission intensity of the complex after sample treatment. Additionally, the kit may further include a display unit that can represent the degree of attenuation in a quantitative or qualitative manner.

Figure 10A:
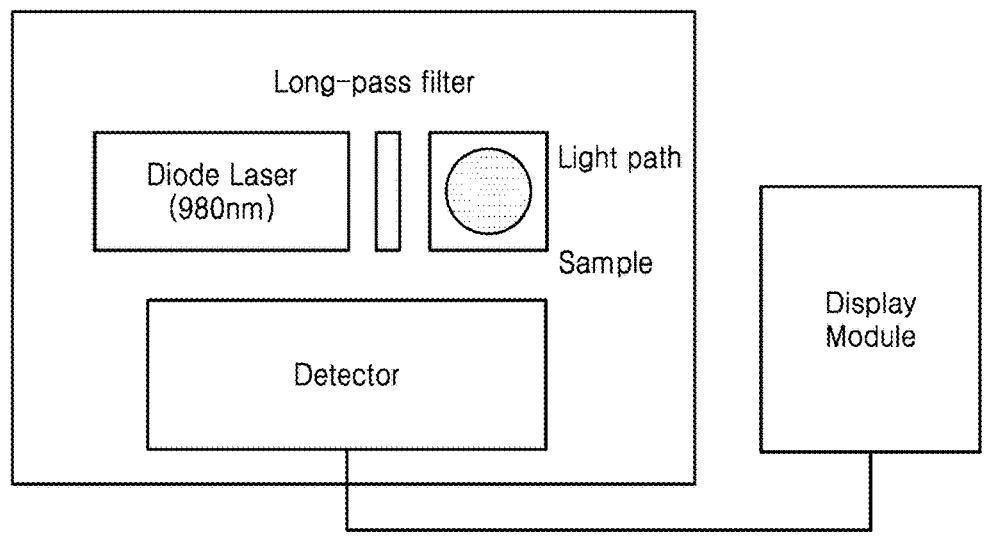
FIG. 10a and FIG. 10b show a schematic plane view and a three-dimensional schematic view for a kit for detecting a target material in accordance with an embodiment of the present disclosure, respectively.
Figure 10B:
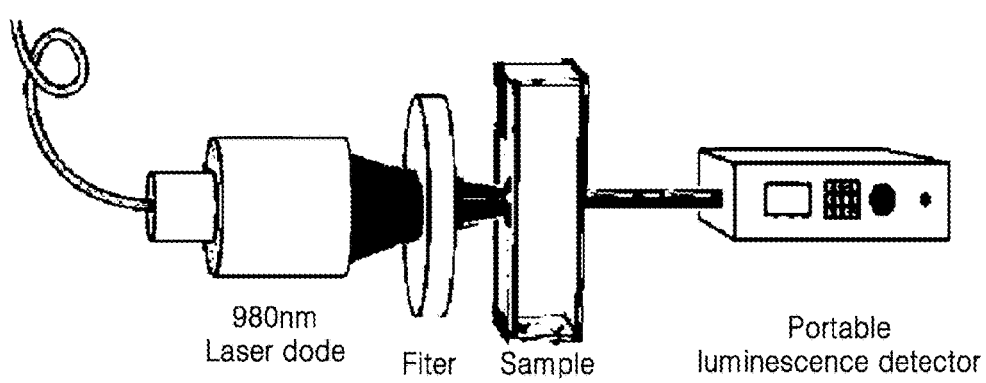

FIGS. 10a and 10b show a schematic plane view and a three-dimensional schematic view for a kit for detecting a target material, respectively.

According to another aspect of the present disclosure, a method of detecting a target material by utilizing the kit is provided. Specifically, the method includes contacting a sample in which a target material is contained with the complex for detecting a target material; and irradiating a near-infrared light source to the complex in contact with the target material in the sample and measuring the degree of attenuation of the eminent signal of the upconverting nanoparticles.

At this time, the sample containing the target material is contacted with the complex in a buffer solution, wherein pH of the sample can be adjusted to optimize the reaction between the complex and the target material, thereby optimizing the degree of attenuation.

The degree of attenuation of the eminent signal that can be optimized by adjusting the length of the linker in the complex for detecting a target material is as discussed above, and therefore the detailed descriptions thereon will be omitted.

Meanwhile, an example of a method of preparing a complex for detecting a target material of the present disclosure, i.e., the upconverting nanoparticles/aptamer-quencher complex will be illustrated as below.

(i) an aptamer-quencher is prepared. The aptamer-quencher may refer to a linker-aptamer-quencher in which the linker is absent or the linker is connected.

(ii) in order to synthesize the upconverting nanoparticles for preparing a complex, a mixed solution of a precursor of the upconverting nanoparticles and a solvent is heat treated, and then cooled to a room temperature. A methanol containing sodium hydroxide and ammonium fluoride is added thereto. Thereafter, the mixture is heat treated under nitrogen gas atmosphere, and reacted over 1 hour, and cooled to a room temperature, and washed with an ethanol to obtain the upconverting nanoparticles.

(iii) The surface of the synthesized upconverting nanoparticles is modified with a carboxyl group. The PEG encapsulation may be carried out to introduce a carboxyl group. PEG-phospholipids is done by mixing the upconverting nanoparticles with 1,2-dimiristoyl-sn-glycero-3-phosphoethanolamine-N-[methoxy(polyethylene glycol)-2000] (mPEG (2000)) and 1,2-distearoyl-sn-glycero-3-phosphoethanol amine-N-[carboxy(polyethanolglycol)-2000] (DSPE-PEG (2000) Carboxylic Acid) and then stirring for 30 minutes. Thereafter, a reaction solvent is evaporated and washed to obtain the upconverting nanoparticles modified with the carboxyl group.

(iv) The chemical bond is formed by a reaction that forms amide bond of the carboxyl group of the upconverting nanoparticles modified with the carboxyl group and a terminal amine group of the (linker)-aptamer-quencher. For example, 1-ethyl-3-(3-dimethylaminopropyl) carbodiimide (EDC) and N-hydroxylsuccinimide (NHS) are added to the modified carboxylated upconverting nanoparticles to react, such that EDC/NHS reaction of 1-ethyl-3-(3-dimethylaminopropyl) carbodiimide (EDC) and N-hydroxylsuccinimide (NHS) can be utilized in the formation of the amide bond.

Hereinafter, preferred Examples of the present disclosure will now be described to provide a further understanding of the present disclosure. However, it should be noted that while the preferred examples are listed for easy understanding of the contents of the present disclosure, the present disclosure is not limited to these examples.

EXAMPLES

Test Example 1

Characteristics of Synthesized Upconverting Nanoparticles 0.78 mmol $YCl_3$ (Yttrium (III) chloride), 0.2 mmol $YbCl_3$ (Ytterbium (III) chloride), and 0.02 mmol $ErCl_3$ (Erbium (III) chloride) were introduced into a mixed solution of 8 mL an oleic acid and 15 mL octadecene, and heat treated up to 160° C. with stirring under nitrogen gas, and then maintained in a vacuum for 30 minutes, and cooled to a room temperature. Then, methanol containing 0.25M sodium hydroxide and 0.4M ammonium fluoride was added. The mixture was heat treated up to 300° C. under nitrogen gas and then continued to react for 1 hour, and cooled back to a room temperature. The precipitate was washed with ethanol to obtain the upconverting nanoparticles.

Figure 2A:
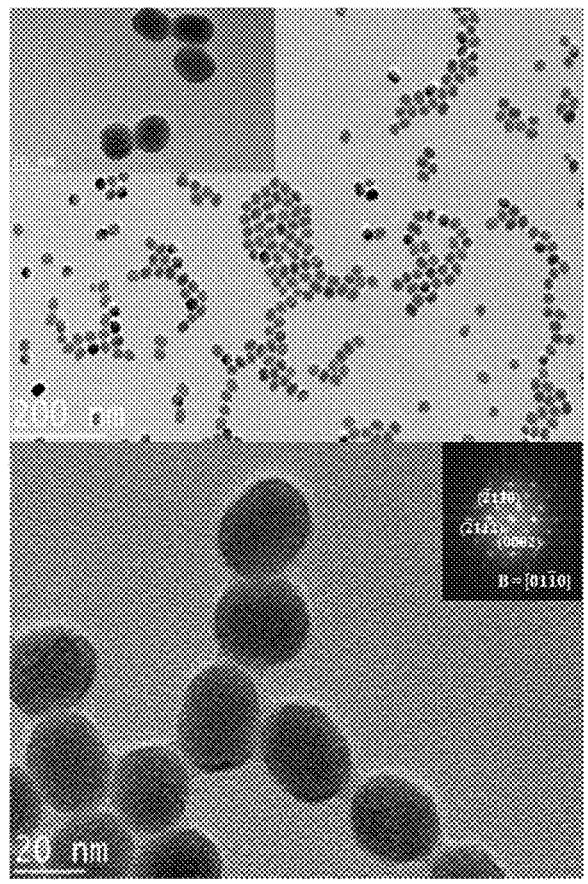
FIG. 2a shows a transmission electron microscope (TEM) image and FIG. 2b shows a size distribution histogram for the upconverting nanoparticles synthesized in accordance with an embodiment of the present disclosure.
Figure 2B:
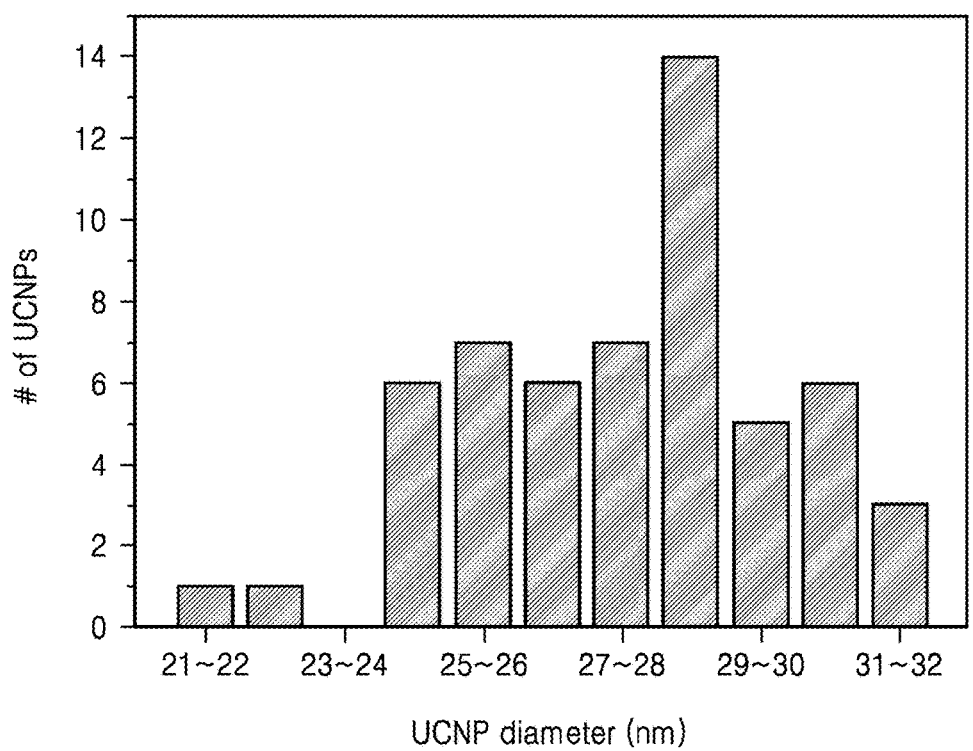

The shapes and sizes of the synthesized upconverting nanoparticles were confirmed using a transmission electron microscope. FIG. 2a shows an image obtained by the transmission electron microscope for the synthesized upconverting nanoparticles and FIG. 2b shows a size distribution histogram for the synthesized upconverting nanoparticles. The upconverting nanoparticles having a rod shape of a hexagonal phase and an average diameter of from about 25 nm to 30 nm were obtained.

In FIG. 3, with respect to the lights emitted upon irradiation of near infrared 980 nm diode laser to the upconverting nanoparticles having a composition comprising $NaYF_4$: 20% $Yb^{3+}$, 2% $Er^{3+}$ as synthesized above (Green emission), the emitted greenish signal images and spectrum having a primary peak at 540-550 nm (green light) could be confirmed using an emission and a fluorescent spectrometer (Manufacturer: Shinco (Korea), model name: FS-2).

Test Example 2

Characteristics of PEG-Encapsulated Upconverting Nanoparticles

Figure 4:
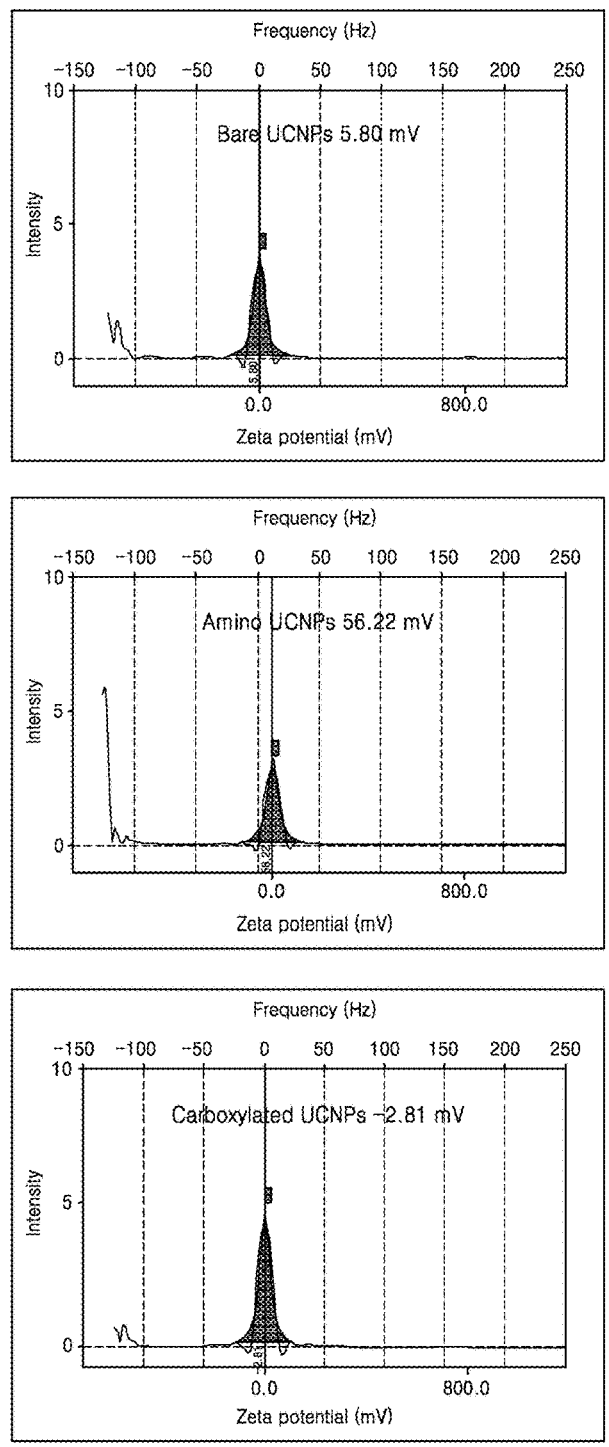
FIG. 4 shows a zeta potential analysis for the upconverting nanoparticles, surface of which is modified with a carboxyl group, synthesized in accordance with an embodiment of the present disclosure.

The synthesized upconverting nanoparticles were modified with carboxyl groups through PEG encapsulation, and then a surface potential was measured using a Zeta-potential analyzer (manufacturer: Photal Otsuka electronics (Japan), model name: ELS Z). The results were shown in FIG. 4. It was confirmed that although the upconverting nanoparticles prior to the modification were at 5.80 mV, after the modification of the upconverting nanoparticles with carboxyl groups, the modified nanoparticles were negatively charged, such as −2.81 mV.

The upconverting nanoparticles were modified with amine groups using 1,2-distearoyl-sn-glycero-3-phosphoethanolamine-N-[amino(polyethanolglycol)-2000] (DSPE- PEG (2000) Amino) instead of 1,2-distearoyl-sn-glycero-3-phosphoethanolamine-N-[carboxy(polyethanolglycol)-2000] (DSPE-PEG (2000) Carboxylic Acid) previously used, then it was confirmed that although the upconverting nanoparticles prior to the modification were at 5.80 mV, after the modification, the modified nanoparticles were positively charged, such as 56.22 mV.

Test Example 3

Figure 5A:
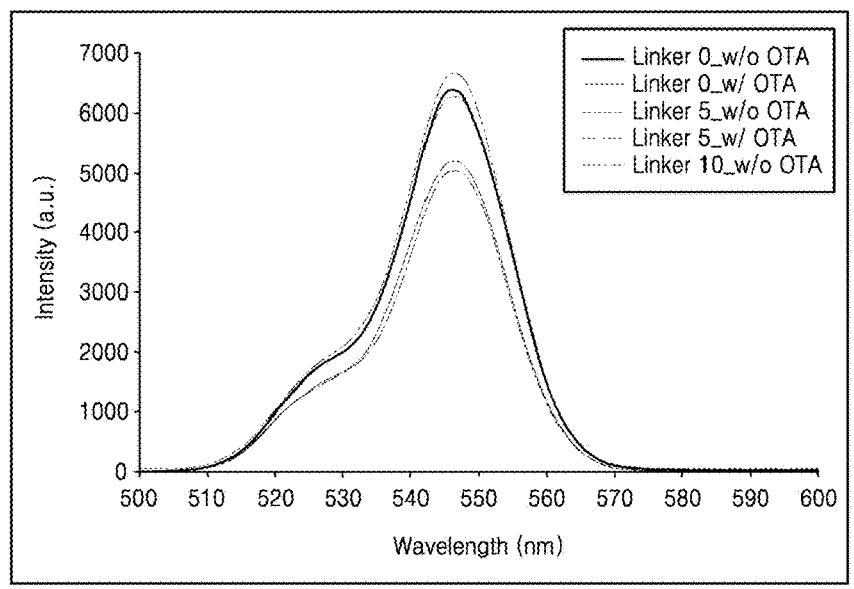
FIG. 5a to FIG. 5c are a graph showing spectra and FIG. 5d is attenuation efficiencies of luminescent signals determined in the presence or absence of target material (Ochratoxin A) for the upconverting nanoparticles/aptamer-quencher complex synthesized by varying the length of a linker in accordance with an embodiment of the present disclosure.
Figure 5B:
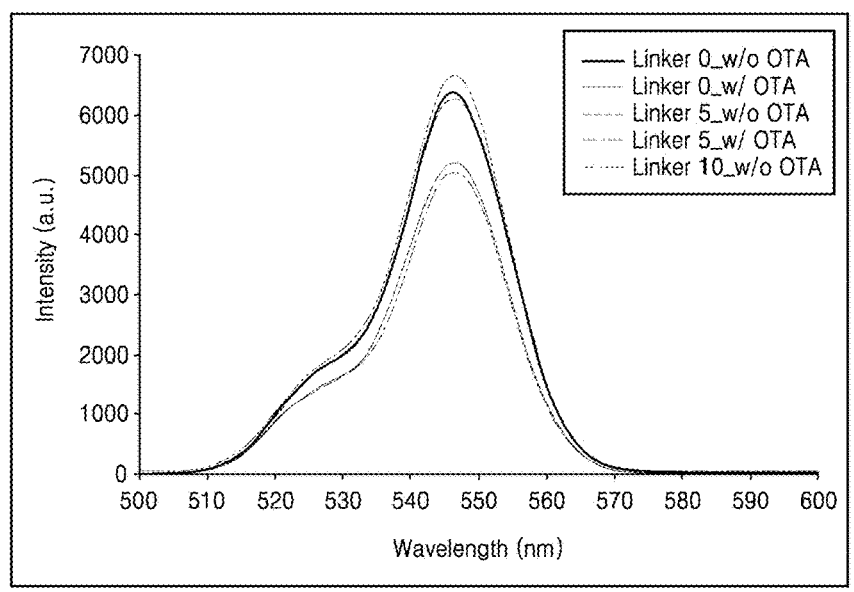
Figure 5C:
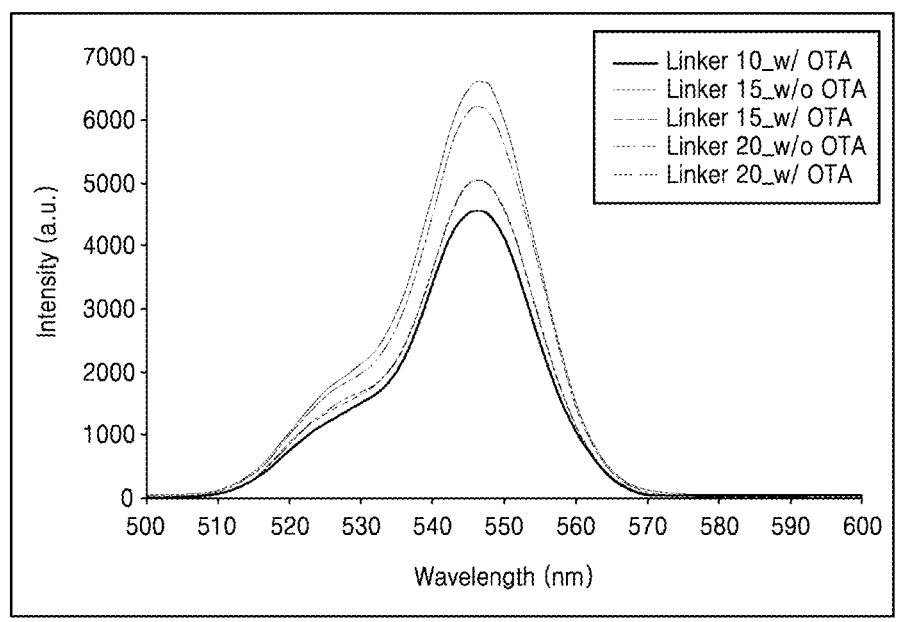
Figure 5D:
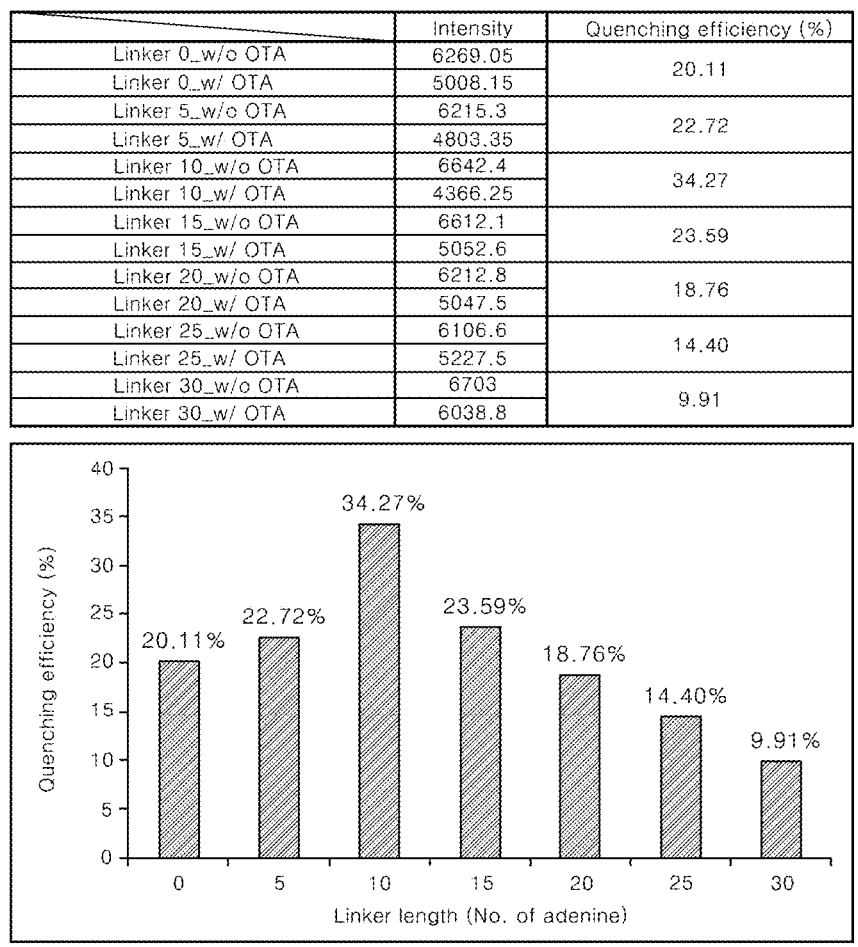

Optimization of Luminescence Resonance Energy Transfer Reactions from Upconverting Nanoparticles to a Quencher in the Synthesized Complex FIG. 5a to FIG. 5c are a graph showing spectra and FIG. 5d is a degree of attenuation efficiencies of the eminent signals attenuated by an luminescence resonance energy transfer in the presence or absence of target material (Ochratoxin A) for upconverting nanoparticles/aptamer-quencher complex synthesized by varying the length of a linker according to the number of the terminal adenine of the aptamer.

The structures of the complexes used herein can be summarized as shown in Table 1 below.

As shown in Table 1, the underlined parts indicate a linker, and the sequences connected following the linker indicate those of the aptamer. The absence of the linker indicates an introduction of an amino-functional group at the 5' terminal portion of the aptamer sequence.

The results of FIG. 6a to FIG. 6d confirmed us that the energy transfer takes place most efficiently with 10 mM Borate buffer at pH 8.5 (reaction conditions: a complex using aptamer-quencher which has 10 adenines, 0.02-fold diluted complex, reacted for 10 minutes in 10 ppb (ng/ml) Ochratoxin).

Figure 7:
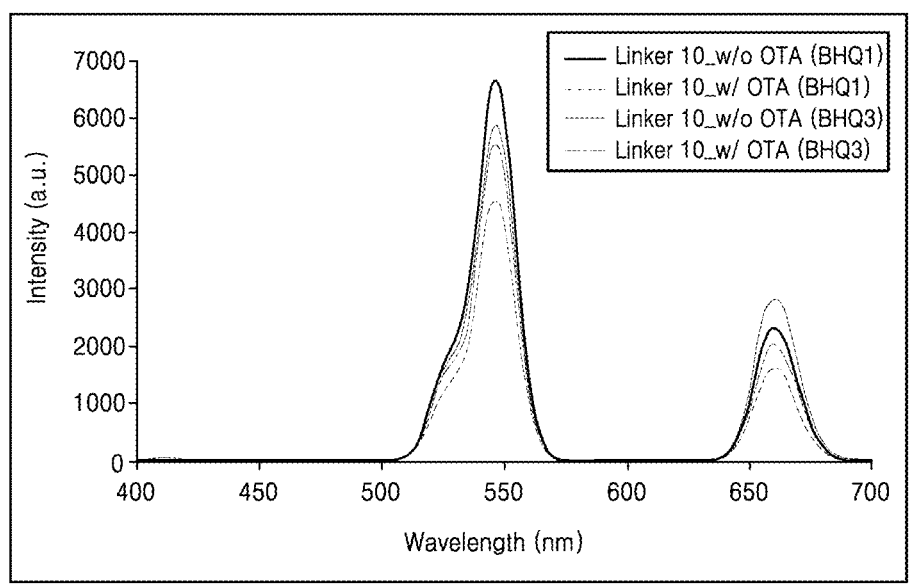
FIG. 7 is a graph showing spectra and attenuation efficiencies of luminescent signals determined in the presence or absence of target material (Ochratoxin A) under different quenchers for the upconverting nanoparticles/aptamer-quencher complex in accordance with an embodiment of the present disclosure.

FIG. 7 is a graph showing spectra and attenuation efficiencies of luminescent signals determined in the presence or absence of target material (Ochratoxin A) for the upconverting nanoparticles/aptamer-quencher complex as synthesized under different quenchers.

BHQ1 and BHQ3 were used as the quencher.

The results of FIG. 7 confirmed us that the quenching efficiency of BHQ1 was 34.27% and the quenching efficiency of BHQ3 was 6.34% at 546.1 nm, and the quenching efficiency of BHQ1 was 29.87% and the quenching efficiency of BHQ3 was 27.08% at 659.7 nm (reaction conditions: a complex using aptamer-quencher which has 10 adenines, 0.02-fold diluted complex, 10 ppb (ng/ml) Ochratoxin, reacted for 10 minutes at 10 mM Tis-HCl (pH 8.8)).

Test Example 4

Figure 8A:
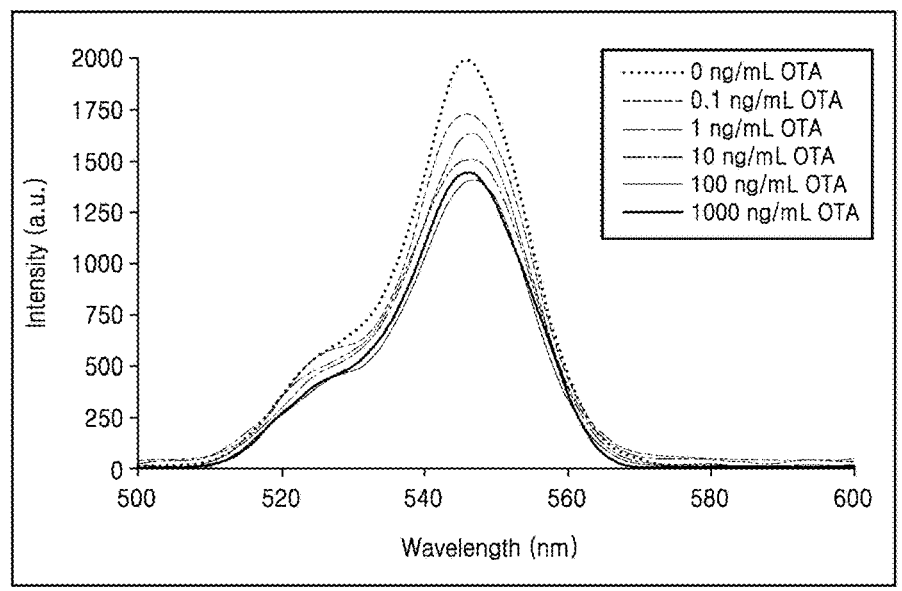
FIG. 8a is a graph showing spectra and FIG. 8b is attenuation efficiencies of luminescent signals determined by varying a concentration of target material (Ochratoxin A) under optimized conditions (length of a linker and pH) for the upconverting nanoparticles/aptamer-quencher complex in accordance with an embodiment of the present disclosure.
Figure 8B:
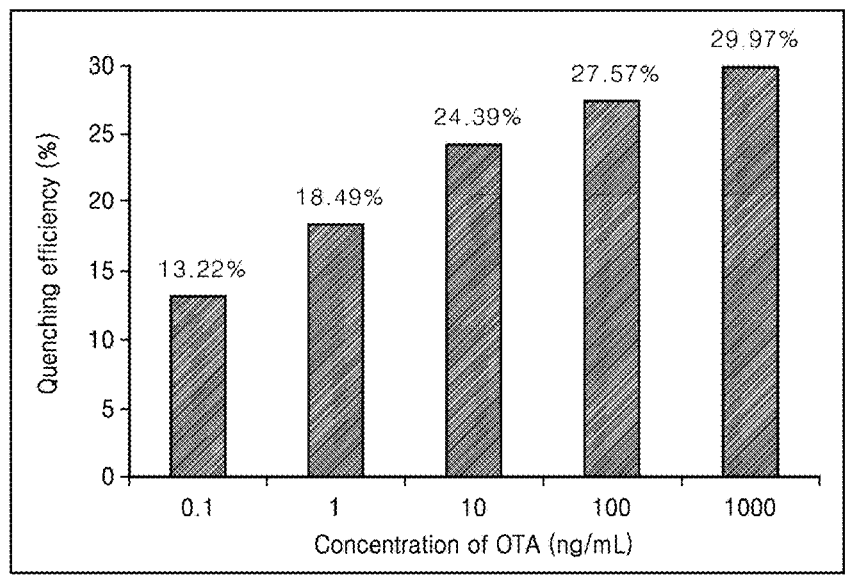

Detection of Mycotoxin Using Luminescence Resonance Energy Transfer of From Upconverting Nanoparticles to a Quencher in the Synthesized Complex FIG. 8a is a graph showing spectra and FIG. 8b is attenuation efficiencies of luminescent signals determined

TABLE 1

| Types | Sequences (5'-3') |
|---|---|
| Amino-0-mer linker-OTA aptamer-BHQ1 | Amino-GCA TCT GAT GGG GTG TGG GTG GCG TAA AGG-BHQ1 |
| Amino-5-mer linker-OTA aptamer-BHQ1 | Amino-AAAAAGCATCTGATCGGGTGTGGGTGGCGTAA AGG-BHQ1 |
| Amino-10-mer linker-OTA aptamer-BHQ1 | Amino-AAAAAAAAAAGCATCTGATCGGGTGTGGGTGGCG TAA AGG-BHQ1 |
| Amino-15-mer linker-OTA aptamer-BHQ1 | Amino-AAAAAAAAAAAAAAAGCATCTGATCGGGTGTGG GTG GCG TAA AGG-BHQ1 |
| Amino-20-mer linker-OTA aptamer-BHQ1 | Amino-AAAAAAAAAAAAAAAAAAAA-GCATCTGATCGGG TGT GGG TGG CGT AAA GG-BHQ1 |
| Amino-25-mer linker-OTA aptamer-BHQ1 | Amino-AAAAAAAAAAAAAAAAAAAAAAAAA-GCATCTG ATC GGG TGT GGG TGG CGT AAA GG-BHQ1 |
| Amino-30-mer linker-OTA aptamer-BHQ1 | Amino-AAAAAAAAAAAAAAAAAAAAAAAAAAAAAA-GCA TCT GAT CGG GTG TGG GTG GCG TAA AGG-BHQ1 |

The results of FIG. 5a to FIG. 5d confirmed us that the energy transfer takes place most efficiently when the number of adenine (A) is 10 (reaction conditions: 0.02-fold diluted complex, 10 ppb (ng/ml) Ochratoxin, reacted for 10 minutes at 10 mM Tis-HCl (pH 8.8)).

Figure 6A:
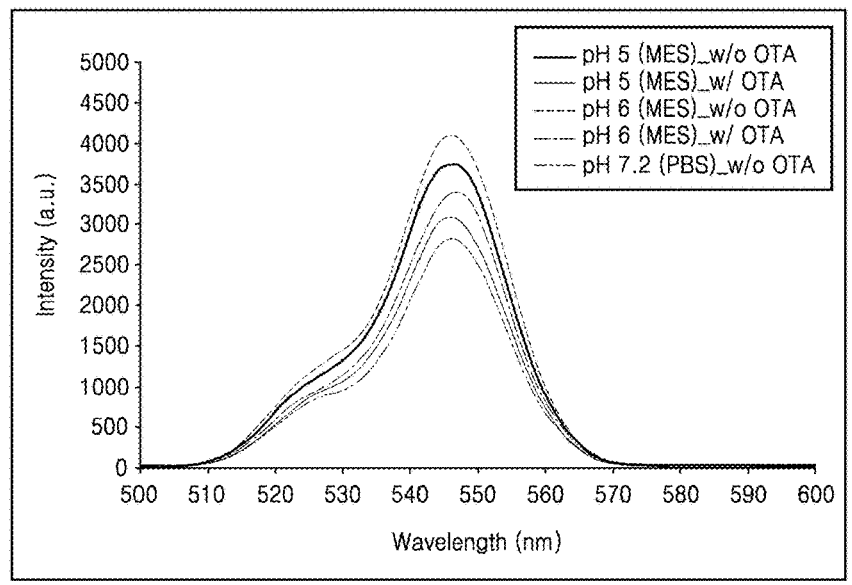
FIG. 6a to FIG. 6c are a graph showing spectra and FIG. 6d is attenuation efficiencies of luminescent signals determined in the presence or absence of target material (Ochratoxin A) under different pH conditions for the upconverting nanoparticles/aptamer-quencher complex in accordance with an embodiment of the present disclosure.
Figure 6B:
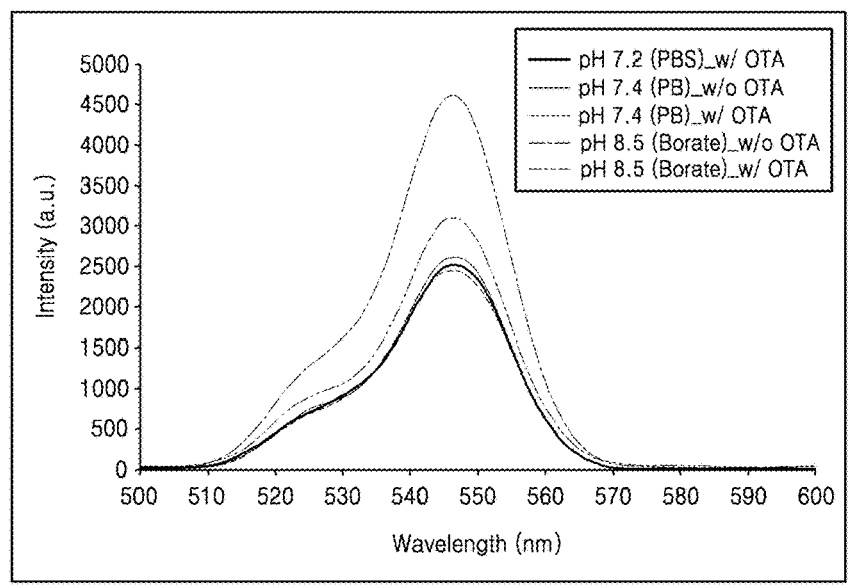
Figure 6C:
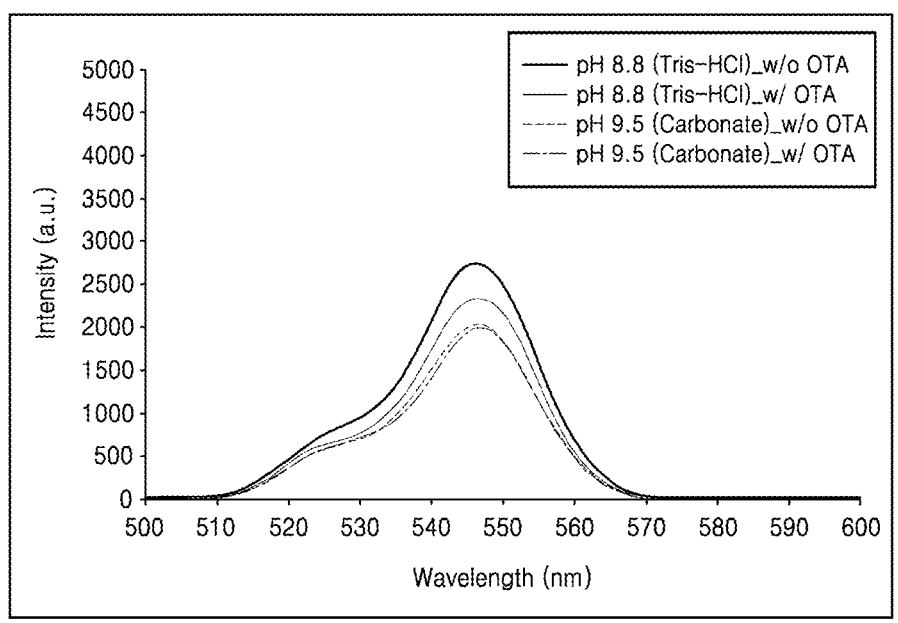
Figure 6D:
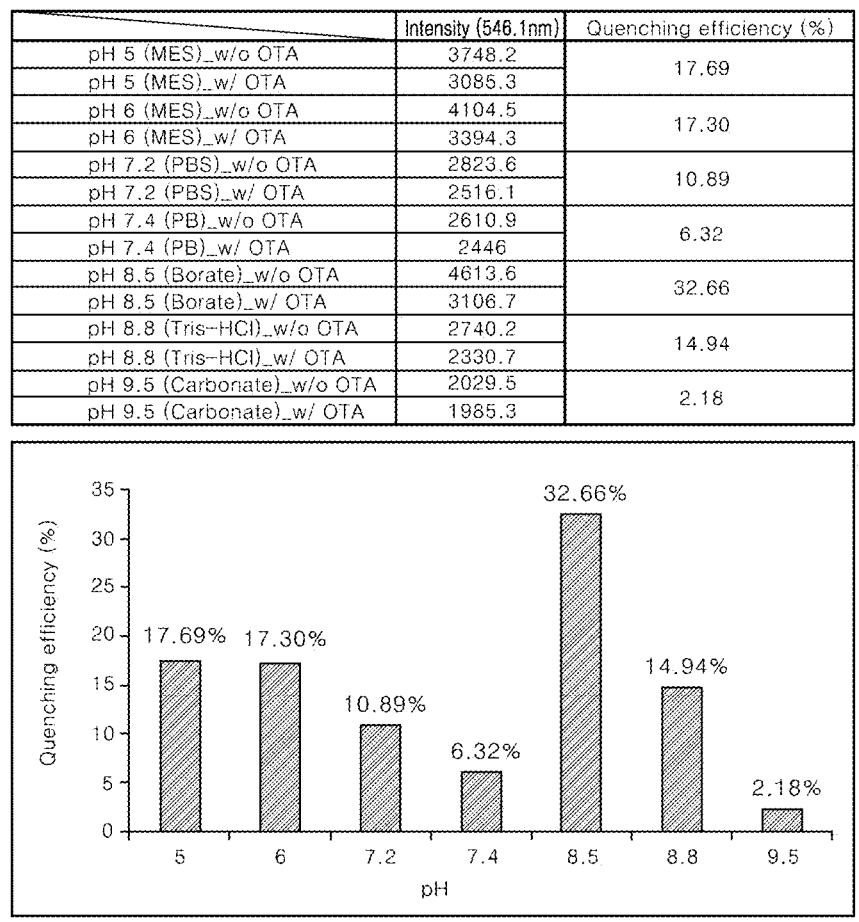

FIG. 6a to FIG. 6c are a graph showing spectra and FIG. 6d is a degree of attenuation efficiencies of luminescent signals determined in the presence or absence of target material (Ochratoxin A) under different pH conditions (buffer compositions) for the upconverting nanoparticles/aptamer-quencher complex as synthesized.

Here, MES (2-(N-morpholino)ethanesulfonic acid), PBS (Phosphate buffered saline), PB (Phosphate buffer), Borate, Tris-HCl, or Carbonate was used as the buffer.

by varying a concentration of target material (Ochratoxin A) under optimized conditions (length of linker and pH) for the upconverting nanoparticles/aptamer-quencher complex.

It could be confirmed that the luminescent intensities in the upconverting nanoparticles of the complex were more and more decreased according to the concentrations of the target mycotoxins (Ochratoxin A). From these results, it could be seen that with the increase of the concentration of Ochratoxin A, the luminescent resonance energy transfer from the upconverting nanoparticles (donor) to the quencher (acceptor) takes place efficiently, whereby the attenuation efficiencies of the eminent signals were increased (reaction conditions: a complex using aptamer-quencher which has 10 adenines, 0.02-fold diluted complex, reacted for 10 minutes at 10 mM Borate (pH 8.5)).

What is claimed is:

1. A complex for detecting mycotoxins, comprising:
   upconverting nanoparticles, wherein the upconverting nanoparticles absorb a light in a near-infrared region and emit an emission signal of an ultraviolet (UV) light or a visible light; and
   an aptamer-quencher, wherein the aptamer-quencher comprises:
      an aptamer, wherein the aptamer is specific for mycotoxins; and
      a quencher, wherein the quencher attenuates the emission signal by absorbing the UV light or the visible light,
   wherein the aptamer-quencher is connected with the upconverting nanoparticles through a linker,
   wherein a binding between the aptamer and the mycotoxins reduces a distance between the upconverting nanoparticles and the quencher, thereby increasing a level of attenuation of the emission signal by the quencher, and
   wherein an emission wavelength region of the upconverting nanoparticles and an absorption wavelength region of the quencher partially or fully overlap with each other.

2. The complex of claim 1, wherein the upconverting nanoparticles and the aptamer-quencher are connected via a physical or chemical bonding between a functional group introduced into the upconverting nanoparticles and a terminal functional group of the linker-aptamer-quencher.

3. The complex of claim 1, wherein the upconverting nanoparticles contain a rare-earth element.

4. The complex of claim 1, wherein the aptamer-quencher is specific to at least one target material.

5. The complex of claim 2, wherein the chemical bonding is an amide bonding between a carboxyl group introduced into a surface of the upconverting nanoparticles and a terminal amine group of the linker-aptamer-quencher.

6. The complex of claim 5, wherein the bonding is done by a reaction between 1-ethyl-3-(3-dimethylaminopropyl) carbodiimide (EDC) and hydroxyl succinimide (NHS).

7. The complex of claim 1, wherein the surface of the upconverting nanoparticles is modified by a silica coating or a polyethylene glycol (PEG) encapsulation.

8. The complex of claim 7, wherein the average diameter of the upconverting nanoparticles is from 25 nm to 30 nm.

9. A method of detecting mycotoxins, comprising:
   connecting a sample with the complex for detecting a target material according to claim 1; and
   irradiating a near infrared light source to the complex in contact with the target material in the sample, and determining a degree of attenuation of eminent signals of the upconverting nanoparticles.

10. The method of claim 9, wherein the degree of attenuation of eminent signals is optimized by adjusting a length of the linker in the complex for detecting a target material.

11. The method of claim 9, wherein the degree of attenuation of eminent signals is optimized by adjusting a pH of the sample.

12. The complex of claim 1, wherein the upconverting nanoparticles comprises at least one selected from the group consisting of yttrium (Y) and ytterbium (Yb), and at least one selected from the group consisting of erbium (Er), holmium (Ho), and thulium (Tm).

13. The complex of claim 1, wherein the upconverting nanoparticles comprises at least one selected from the group consisting of $NaYF_4$: 20% $Yb^{3+}$, 2% $Er^{3+}$, $NaYF_4$: 20% $Yb^{3+}$, 2% $Ho^{3+}$, and $NaYF_4$: 20% $Yb^{3+}$, 2% $Tm^{3+}$.

14. The complex of claim 1, wherein the aptamer is specific for Ochratoxin A.

15. The complex of claim 1, wherein the linker connecting the upconverting nanoparticles and the aptamer-quencher is an oligonucleotide sequence having a length ranging from 5 to 15 nucleotides.

* * * * *